(12) United States Patent
Norred et al.

(10) Patent No.: US 9,550,014 B2
(45) Date of Patent: Jan. 24, 2017

(54) POSTPARTUM UTERINE CONTRACTILE APPARATUS AND METHOD

(75) Inventors: Alex James Norred, San Luis Obispo, CA (US); George Cochran Harper, Laguna Niguel, CA (US); David Lagrew, Irvine, CA (US); Davis Reed Carlin, San Luis Obispo, CA (US); Jan Segnitz, San Luis Obispo, CA (US); Amelia Michele Degenkolb, San Luis Obispo, CA (US)

(73) Assignee: InPress Technologies, Inc., San Luis Obispo, CA (US)

( * ) Notice: Subject to any disclaimer, the term of this patent is extended or adjusted under 35 U.S.C. 154(b) by 890 days.

(21) Appl. No.: 13/420,871

(22) Filed: Mar. 15, 2012

(65) Prior Publication Data

US 2013/0245581 A1 Sep. 19, 2013

(51) Int. Cl.
*A61M 1/00* (2006.01)
*A61B 17/42* (2006.01)
*A61B 17/12* (2006.01)

(52) U.S. Cl.
CPC ............ *A61M 1/0088* (2013.01); *A61B 17/42* (2013.01); *A61B 17/12099* (2013.01); *A61B 17/12136* (2013.01); *A61B 2017/12004* (2013.01); *A61B 2017/4216* (2013.01); *A61B 2217/005* (2013.01); *A61M 1/0049* (2013.01); *A61M 2205/0266* (2013.01); *A61M 2210/1433* (2013.01)

(58) Field of Classification Search
CPC .. A61M 27/00; A61M 27/002; A61M 27/006; A61M 27/008; A61M 25/00; A61M 25/0015; A61M 25/0021; A61M 25/0029; A61M 25/003; A61M 25/10; A61M 25/10184; A61M 2025/0024; A61M 2025/0025; A61M 31/00; A61M 1/0001; A61M 1/0005; A61M 1/0013; A61M 1/0019; A61M 1/0023; A61M 1/0088; A61M 1/009; A61M 1/0094; A61M 2001/0017
See application file for complete search history.

(56) References Cited

U.S. PATENT DOCUMENTS

| | | | |
|---|---|---|---|
| 2,185,927 A | | 1/1940 | Shelanski |
| 2,981,255 A | * | 4/1961 | Heyns ............................ 606/123 |
| 3,517,665 A | | 6/1970 | Sheldon |
| 3,670,732 A | | 6/1972 | Robinson |
| 3,774,613 A | * | 11/1973 | Woods et al. ................. 604/128 |
| 3,828,781 A | | 8/1974 | Rothman |
| 4,563,183 A | | 1/1986 | Barrodale et al. |

(Continued)

FOREIGN PATENT DOCUMENTS

| | | |
|---|---|---|
| CN | 2933317 Y | 8/2007 |
| JP | 05305145 | 11/1993 |

(Continued)

*Primary Examiner* — Tan-Uyen (Jackie) T Ho
*Assistant Examiner* — Ned T Heffner
(74) *Attorney, Agent, or Firm* — Jeffrey Schox; Ivan Wong

(57) ABSTRACT

A uterine contractile device includes a series of perforated tubes, a sealing balloon, and an additional connecting tube to deliver a vacuum force inside the lumen of a postpartum uterus. The uterine contractile device may be used after child birth to facilitate contraction of a woman's uterus. By facilitating contraction of the uterus, a medical professional may achieve immediate and sustained hemostasis of the mother.

9 Claims, 12 Drawing Sheets

(56) References Cited

U.S. PATENT DOCUMENTS

| | | | |
|---|---|---|---|
| 4,784,654 A | | 11/1988 | Beecher |
| 4,925,452 A | * | 5/1990 | Melinyshyn .......... A61M 25/00 138/111 |
| 4,955,875 A | | 9/1990 | Knowles |
| 5,100,395 A | * | 3/1992 | Rosenberg .................... 604/284 |
| 5,104,377 A | * | 4/1992 | Levine .................... 604/101.05 |
| 5,242,438 A | * | 9/1993 | Saadatmanesh et al. ....... 606/15 |
| 5,464,409 A | | 11/1995 | Mohajer |
| 5,603,685 A | | 2/1997 | Tutrone |
| 5,769,880 A | * | 6/1998 | Truckai et al. ............... 607/101 |
| 6,506,149 B2 | | 1/2003 | Peng et al. |
| 6,641,575 B1 | | 11/2003 | Lonky |
| 6,676,680 B1 | | 1/2004 | Packer |
| 9,125,686 B2 | | 9/2015 | Norred et al. |
| 2002/0010457 A1 | * | 1/2002 | Duchon et al. ............... 604/515 |
| 2003/0191452 A1 | | 10/2003 | Meglin et al. |
| 2007/0032814 A1 | | 2/2007 | Hibler |
| 2007/0149998 A1 | | 6/2007 | Wicks et al. |
| 2008/0051708 A1 | * | 2/2008 | Kumar et al. ................ 604/119 |
| 2010/0069886 A1 | | 3/2010 | Wilkes |
| 2010/0228239 A1 | | 9/2010 | Freed |
| 2011/0098524 A1 | | 4/2011 | Barcelo Rojas |
| 2011/0208178 A1 | | 8/2011 | Truckai |

FOREIGN PATENT DOCUMENTS

| | | |
|---|---|---|
| KR | 20010002164 A | 1/2001 |
| RU | 2440038 C2 | 1/2012 |
| SU | 1426560 A1 | 9/1988 |
| WO | 2011097350 A1 | 8/2011 |

\* cited by examiner

US 9,550,014 B2

POSTPARTUM UTERINE CONTRACTILE APPARATUS AND METHOD

BACKGROUND

Postpartum hemorrhage, defined as excessive blood loss after birth, is the leading cause of maternal death in the world, claiming the lives of over 125,000 mothers every year. Inability to control postpartum bleeding can require a woman to receive multiple blood transfusions, and in severe cases, a full hysterectomy. Accordingly, it is desirable to control such postpartum bleeding, if possible, at its onset. The cause of postpartum hemorrhage, in approximately 80% of cases, is uterine atony, which is the inability of the woman's uterus to contract after delivering the child. Risk factors for uterine atony include prolonged staged of labor, preeclampsia, and multiparity.

The original technology for treating postpartum hemorrhage was oxytoxic agents, hormonal agents that induce muscle contraction. Unfortunately, studies have increasingly shown that oxytoxic agents do not significantly reduce either the incidence of postpartum hemorrhage or the amount of blood lost. Some studies have even indicated that oxytoxic agents are being over used to the point that this treatment increases the risk of uterine atony.

Other approaches have been taken, such as medical devices. U.S. Pat. No. 4,552,557 discloses a inflatable intrauterine device that inflates intrauterinely, acting a tamponade to stop blood flow. Because this device expands when inflated, this device and method do not facilitate uterine contraction. U.S. Patent Publication No. 2011/0087337 discloses a generic organ contraction device for controlling the flow of fluid in a lumen formed by a tissue wall of a patient's organ, however this device does not use suction to contract the organ. Finally, U.S. Patent Publication No. 2011/0172569 discloses a surgical vacuum device that uses a suction cup to tamponade specific surfaces of an organ. However, the suction cup is not capable of contracting a uterus.

Dr. Christopher B. Lynch has developed a technique for surgically removing the uterus, wrapping the uterus in sutures, and pulling on these sutures to contract the uterus. Although this approach has been effective at arresting postpartum hemorrhage this method is extremely invasive and potentially very harmful to the patient. What is needed is a device that can contract a postpartum uterus in a non-invasive manner.

SUMMARY OF THE INVENTION

The present invention provides a transvaginally-delivered uterine contractile device that provides a vacuum to the uterus which stops hemorrhaging, removes blood from the uterus and causes the uterus to contract. In an embodiment, the uterine contractile device comprises a plurality of porous, flexible medical-grade tubes that allow for delivery of the vacuum to the uterine lumen. Additionally, the uterine contractile device seals the uterus off from atmospheric pressure using an occlusion balloon that engages the inner surface of the distal end of the vaginal canal. Once inserted into the uterus, the occlusion balloon can be inflated to create a seal with the vaginal canal. The device may then be connected to a medical-grade pump with a tissue and blood filter. The pump can apply a vacuum to the device which removes fluids from the uterus and causes the uterus to contact around the device.

By contracting a woman's postpartum uterus with the inventive device, a medical professional can immediately stop hemorrhaging and blood loss from the uterus after child birth. This reduces a wide range of risks to mother while in the hospital, including the need for blood transfusions or hysterectomy. Furthermore, because the device is delivered transvaginally, the mother can remain conscious during the procedure. Medical professionals can also leave the device in the patient with minimal monitoring necessary. The use of a vacuum furthermore provides a uniform mechanical stimulus to the walls of the postpartum uterus, facilitating an even contractile movement of the tissue.

DETAILED DESCRIPTION

Figure 1:
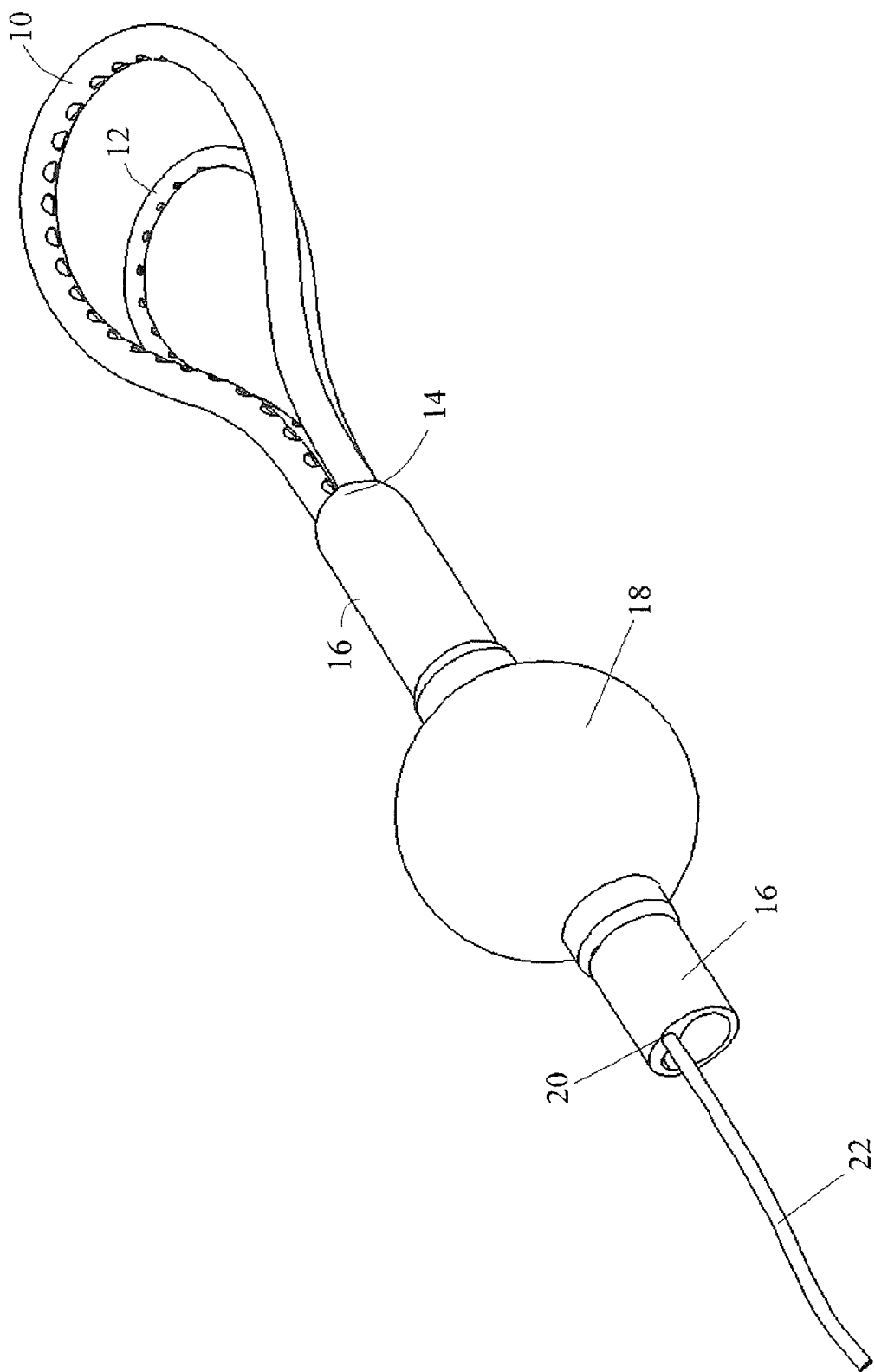
FIG. 1 is a perspective view of an embodiment of the uterine contractile device.

A first embodiment of the uterine contractile device is illustrated in FIG. 1. In this embodiment, the uterine contractile device has a plurality of curved tubes 10, 12 that attach to the base 14 of a larger connecting tube 16. This connecting tube 16 passes through a sealing balloon 18. In this embodiment of the device, the sealing balloon 18 is inflated via a channel 20 inside the connecting tube by some external fluid source via an attached fluid tube 22. In an embodiment, a compressible gas such as nitrogen or air can be used to inflate the sealing balloon 18. Alternatively, in other embodiments, any other fluid source or mechanism can be used to inflate the sealing balloon 18. The uterine contractile device is intended to be partially placed within a woman's body with the curved tubes 10, 12 inside the woman's atonic uterus, while the connecting tube 16 and surrounding occlusion balloon are oriented inside the vagina.

In the embodiment illustrated in FIG. 1, the uterine contractile device contains two tubes 10, 12 that are both arranged in loops that extend different distances. The outer tube 10 can have a larger length and extend in a wider loop away from the device and the inner tube 12 can have a shorter length and be configured in a loop that is within the wider loop of the outer tube 10. The tubes 10, 12 may be of the same or differing cross section diameters. In a preferred embodiment, the outer diameters of the tubes 10, 12 may be as small as 25 mm and as large as 125 mm. The number of tubes may exceed two, but in a preferred embodiment, there should be no more than eight tubes extending from the uterine contractile device. The outer cross sectional shape of the tubes 10, 12 should be substantially rounded to prevent abrasion and allow for greater acceptance by the native tissue.

The tubes 10, 12 can be composed of a flexible material that allows the tubes 10, 12 to be bent in any direction which also allows the tubes 10, 12 to conform as necessary to any woman's anatomy. However, the tube 10, 12 material and construction also preferably provide sufficient rigidity to maintain a fixed angle with the connecting tube 16. The tubes 10, 12 are preferably composed of a material appropriate for medical applications, including but not limited to: rubber, plastic, silicone, silastic, polyethylene, polyurethane, other plastic(s) or metal(s) or any other suitable materials. These materials can be used alone or in combination with each other. In an embodiment, the curved perforated tubes 10, 12 may be made of an elastic material having a Shore A hardness of about 60-80 and the connecting tube 16 may have a Shore A hardness of about 70-90.

Figure 2:
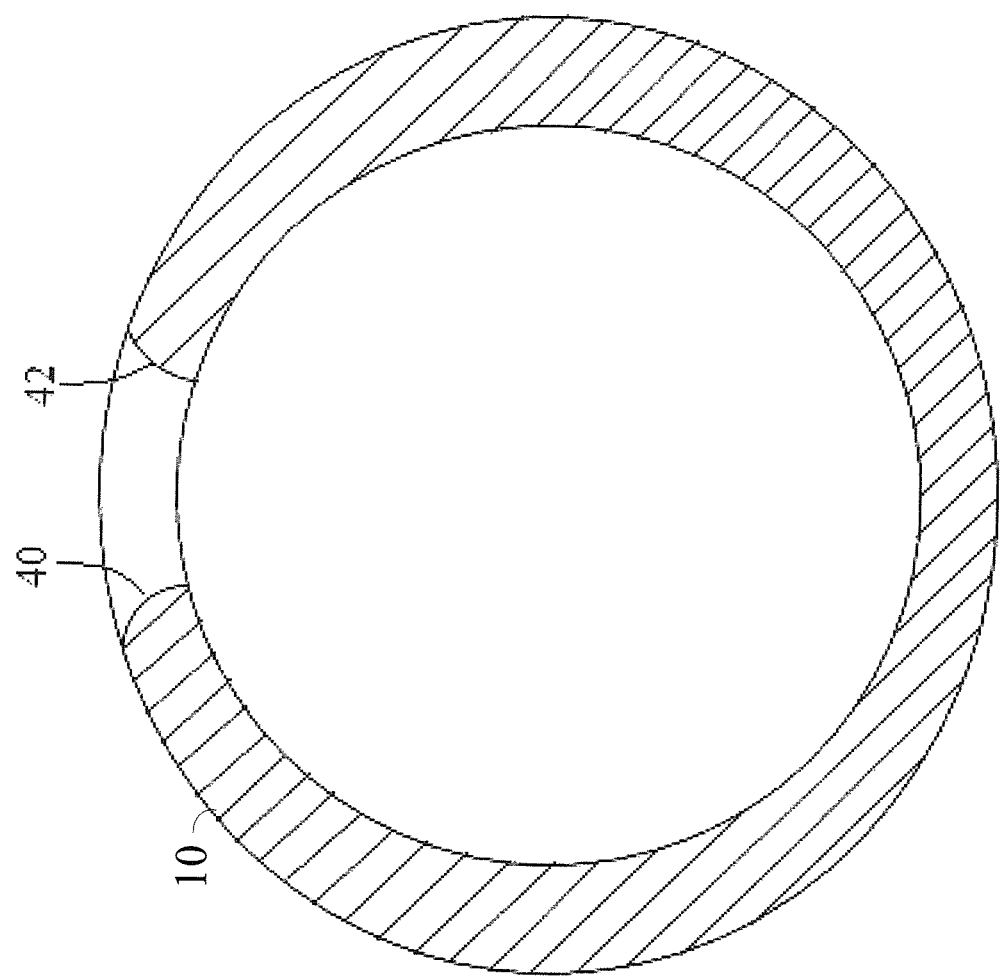
FIG. 2 is a cross sectional view of and embodiment of the perforated tubing portion of the uterine contractile device.

A cross sectional view of a perforated portion of the tube 10 is illustrated in FIG. 2. Each tube 10 has in interior space that can be connected to a plurality of perforations. When a vacuum is applied to the interior of the tube, the vacuum can cause fluids including blood, water and other fluids to flow from the interior of the woman's uterus adjacent the exterior of the tube 10 through the perforations and into the interior volume of the tube 10. The vacuum can also cause the uterus to contract around the tube 10.

The perforations 40 in the tube 10 can be round holes with rounded exterior edges that may be formed in one or more sides of the tubing. However, it is preferable that these perforations 40 be on the medial sides of the tubing 10, reducing their direct contact with tissue. The interior edge 42 of the perforation 40, in addition the shape for the perforation 40, can be substantially rounded, to allow for better interaction with tissue. These rounded edges provide a safety feature for the device. For example, if the edge of the perforation 40 was a sharp edge, the vacuum might suck the interior of the uterus against the sharp edge of the perforation 40 damaging the uterus. In an embodiment, the perforations may have a diameter between about 0.1-0.6 cm. The inner diameter of the tube 10 can be between about 0.25-1.00 cm and the outer diameter of the tube 10 can be between about 0.50 to 1.25 cm.

Figure 3:
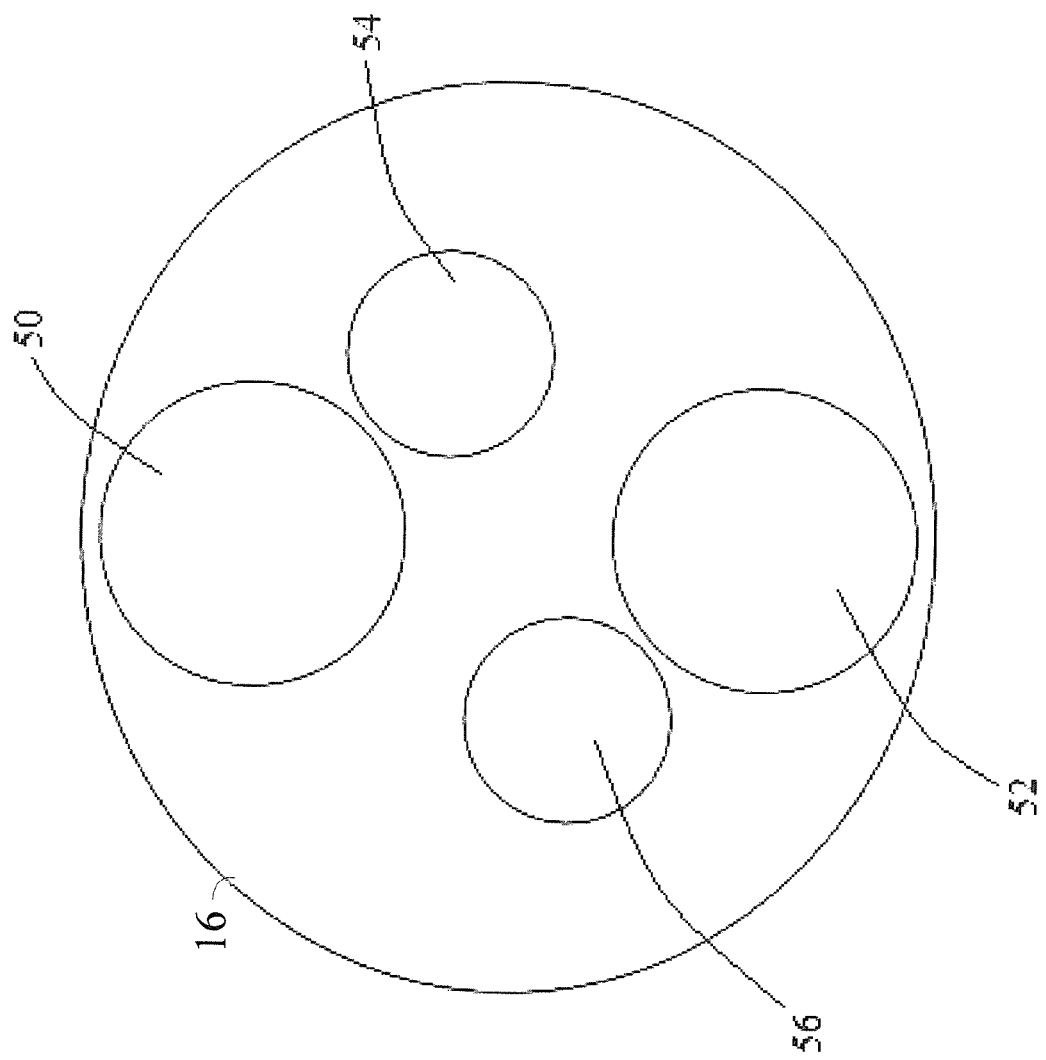
FIGS. 3 and 4 are cross sectional views of different embodiments of the perforated tubes to the connecting tube connection portion of the uterine contractile device.
Figure 4:
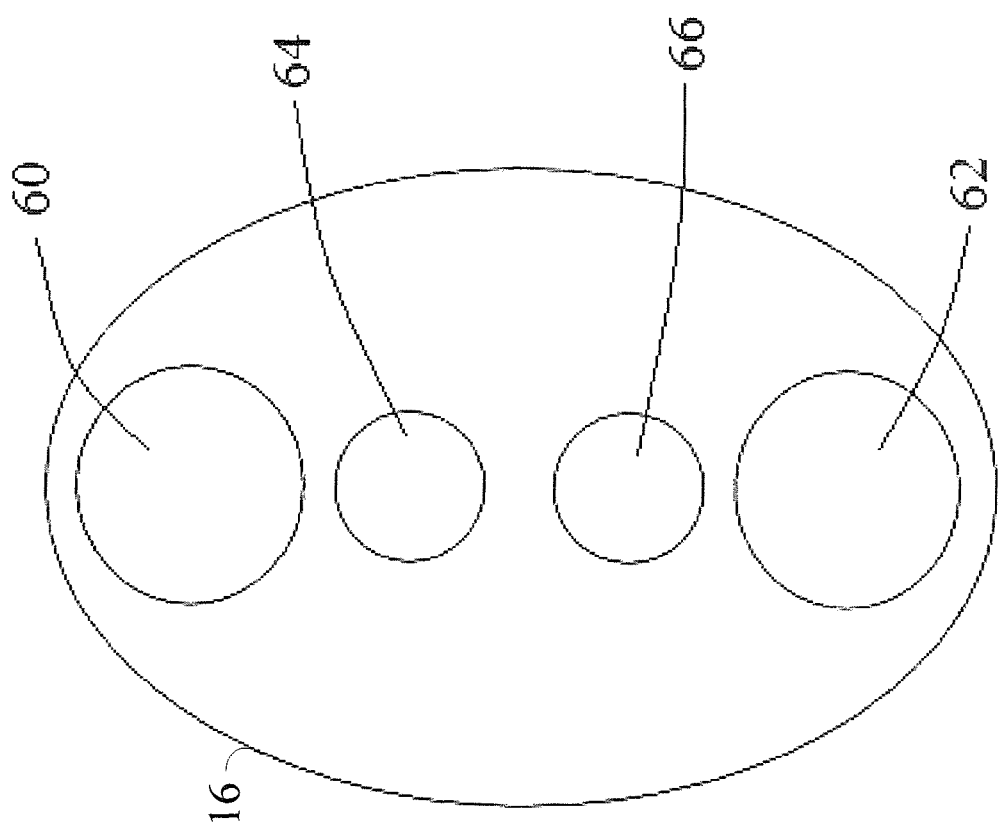

A top view of an embodiment of an attachment structure for connecting the tubes to the end of the connecting tube 16 is illustrated in FIG. 3. Ideally, the attachment structure is a single piece structure. However in other embodiments, other devices and methods for tube attachment are possible. In FIG. 3, the tubing attachments are offset from each other, allowing the larger attachments 50 and 52 to fit next to the smaller attachments 54 and 56. FIG. 4 illustrates an alternate structure for attachment of the tubes to the end of the connecting tube 16, wherein the outer, larger tube attachments 60 and 62 are directly in line with the inner, smaller tube attachments 64 and 66, and the cross section of the entire attachment is more elliptical than circular.

Figure 5:
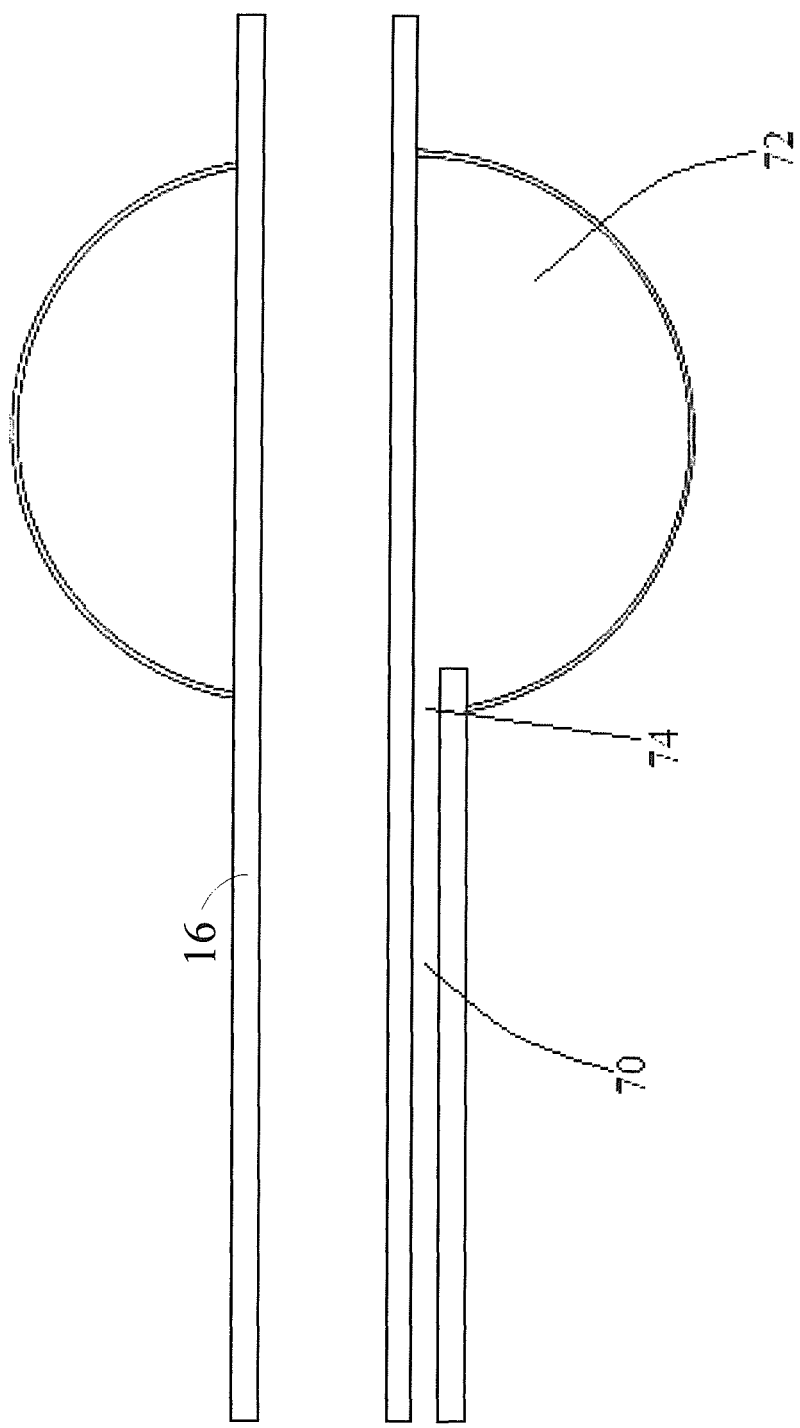
FIG. 5 is a side cross sectional view of an embodiment of the connecting tube and surrounding occlusion sealing balloon.

FIG. 5 illustrates a side cross sectional view of an embodiment of the sealing balloon 72 that surrounds the connecting tube 16. A channel 70 can be used to deliver a sterile fluid such as saline to the lumen of the balloon 72 at opening 74. In other embodiments, any other type of sterile fluid or compressible gas can be used to inflate the balloon 72. The total inflated volume should be substantially large enough to fill the entire cross section of the entrance of the woman's postpartum uterus, which can be 300-400 milliliters or more. The length of the balloon 72 may be between 5.0 and 10.0 cm in length. The outer diameter of the connecting tube 16 can be between about 1.5-3.0 cm. The inner diameter of the connecting tube 16 which is the suction lumen can be between about 1.2-2.7 cm and the inner diameter of the channel 70 which is the balloon inflation lumen can be between about 0.2-0.4 cm and the outer diameter of the channel 70 can be between about 0.25-0.50. As discussed, the material of the connecting tube 16 may be composed of rubber, plastic, silicone, silastic, plastic, polyethylene, and polyurethane or any other suitable material. The preferred material is silicone.

Figure 6:
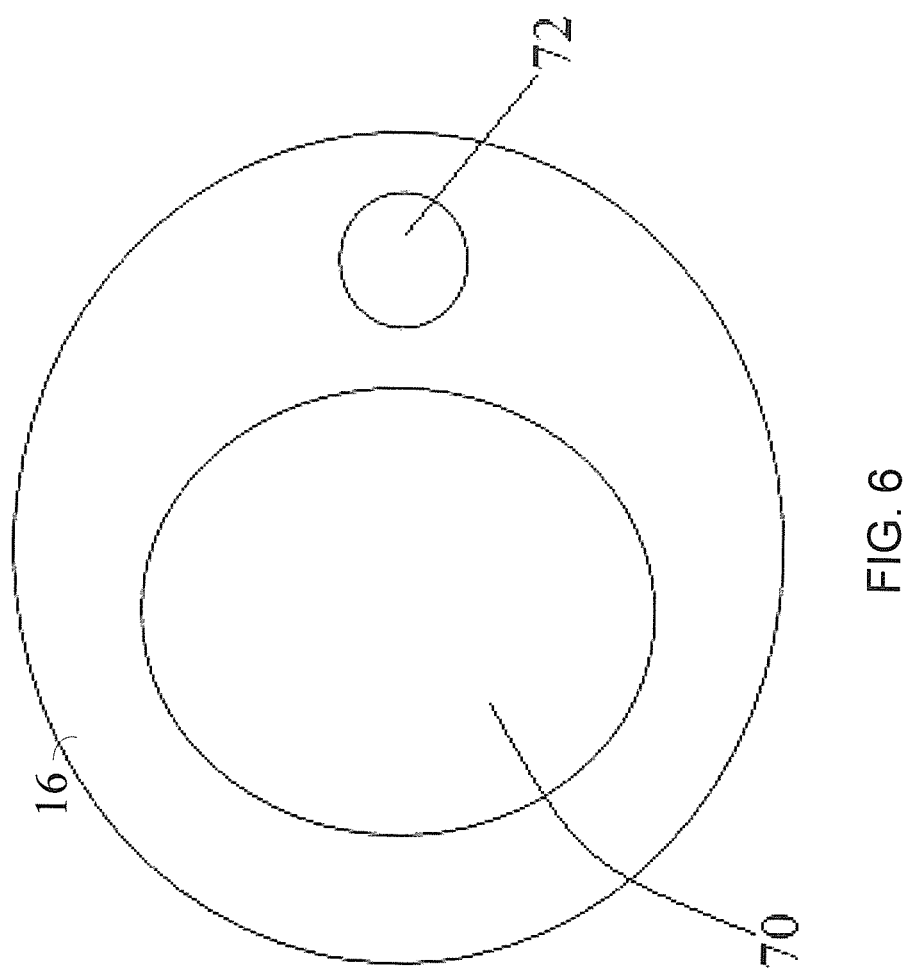
FIG. 6 is a cross sectional view of an embodiment of the connecting tube of the uterine contractile device having a smaller lumen for the delivery of a fluid to the occlusion sealing balloon.
Figure 7:
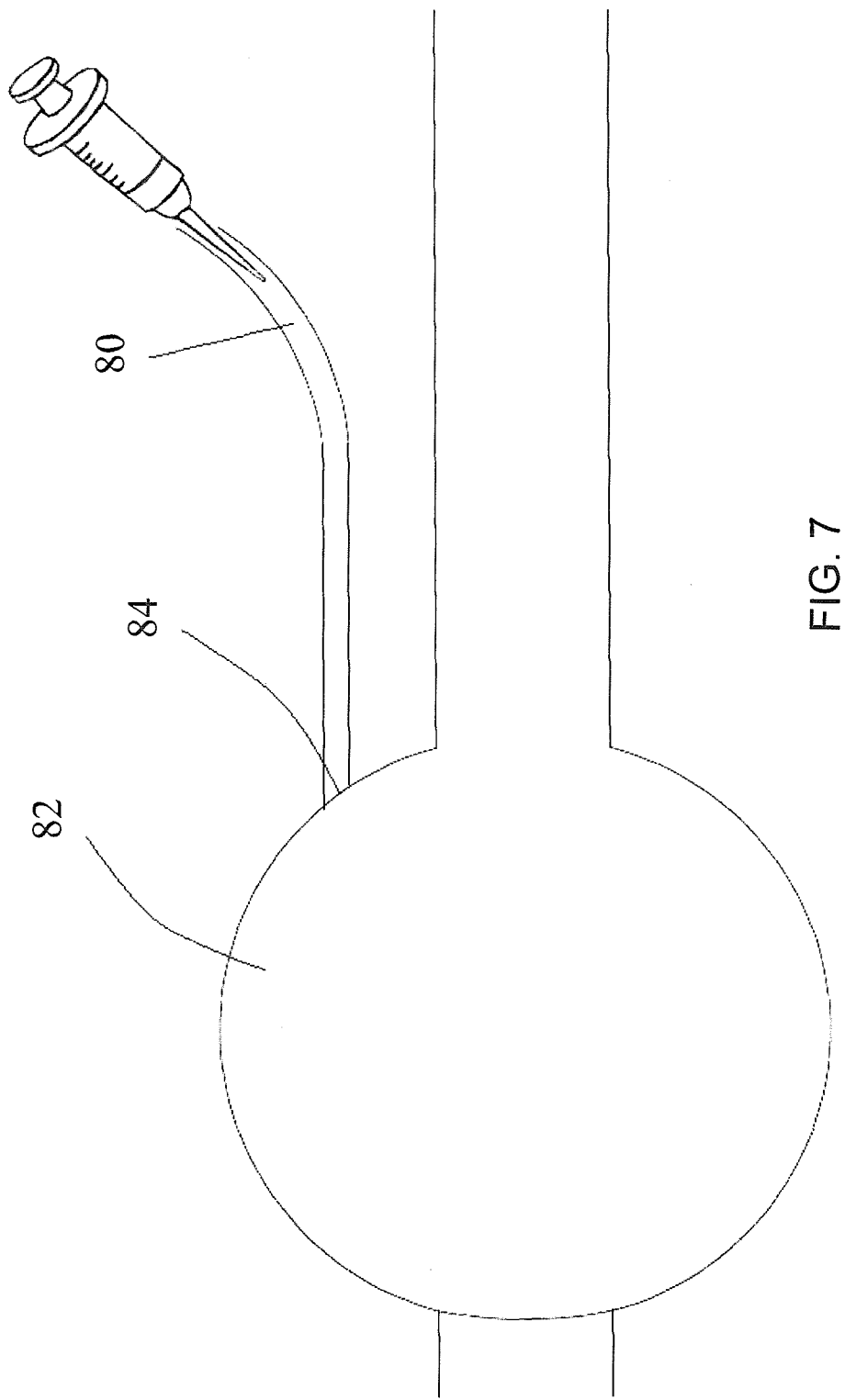
FIG. 7 is a top view of an alternative embodiment of the uterine contractile device that includes a mechanism for delivering fluid to the occlusion sealing balloon.

FIG. 6 illustrates a cross sectional view of an embodiment of the connecting tube 16. The larger lumen 70 delivers the vacuum of the device. The smaller lumen 72 delivers the sterile fluid such as saline the sealing balloon. FIG. 7 illustrates a top view of an alternate method of inflating the sealing balloon. The external tube 80 delivers the sterile fluid to the sealing balloon 82 through a sealed opening in the balloon 84.

The material of the connecting tube may be composed of rubber, plastic, silicone, silastic, plastic, polyethylene, polyurethane, and one or more metals or any other suitable material or combination of materials. The preferred material is silicone.

Figure 8:
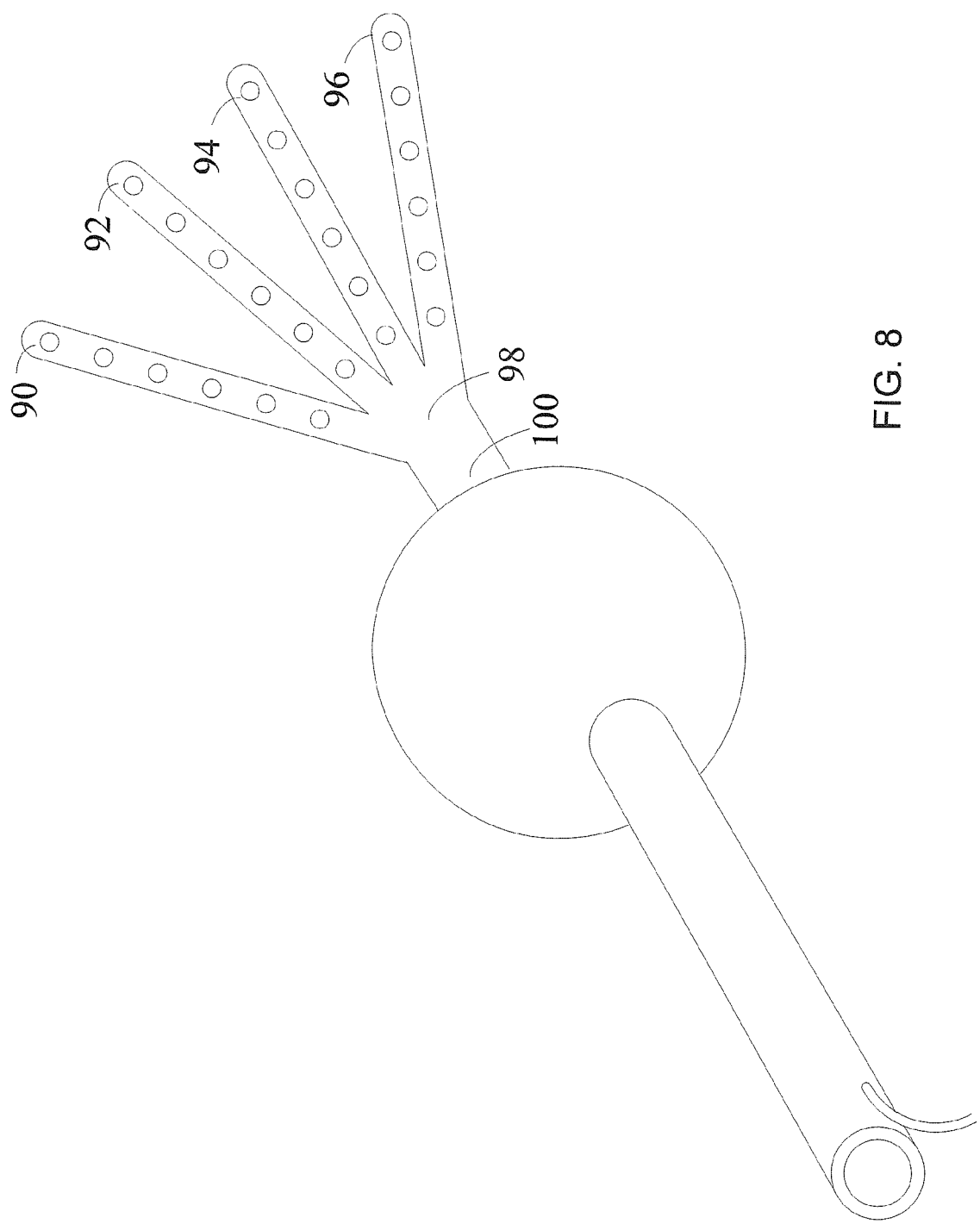
FIG. 8 is a perspective view of an embodiment of the uterine contractile device wherein the perforated tubing is configured as elongated members rather than a loop extending from the connecting tube.

FIG. 8 illustrates an alternate embodiment of the device (perspective view). In this embodiment, the array of tubes 90, 92, 94, and 96 do not bend around to the point of attachment 98 of the connecting tube 100. Preferably, there should be no more than sixteen tubes in the array. The tips of these tubes should be substantially rounded and the exterior surfaces of the tubes 90, 92, 94, and 96 should not have any sharp edges to prevent injury to the patient and allow for better interaction with tissue.

Figure 9:
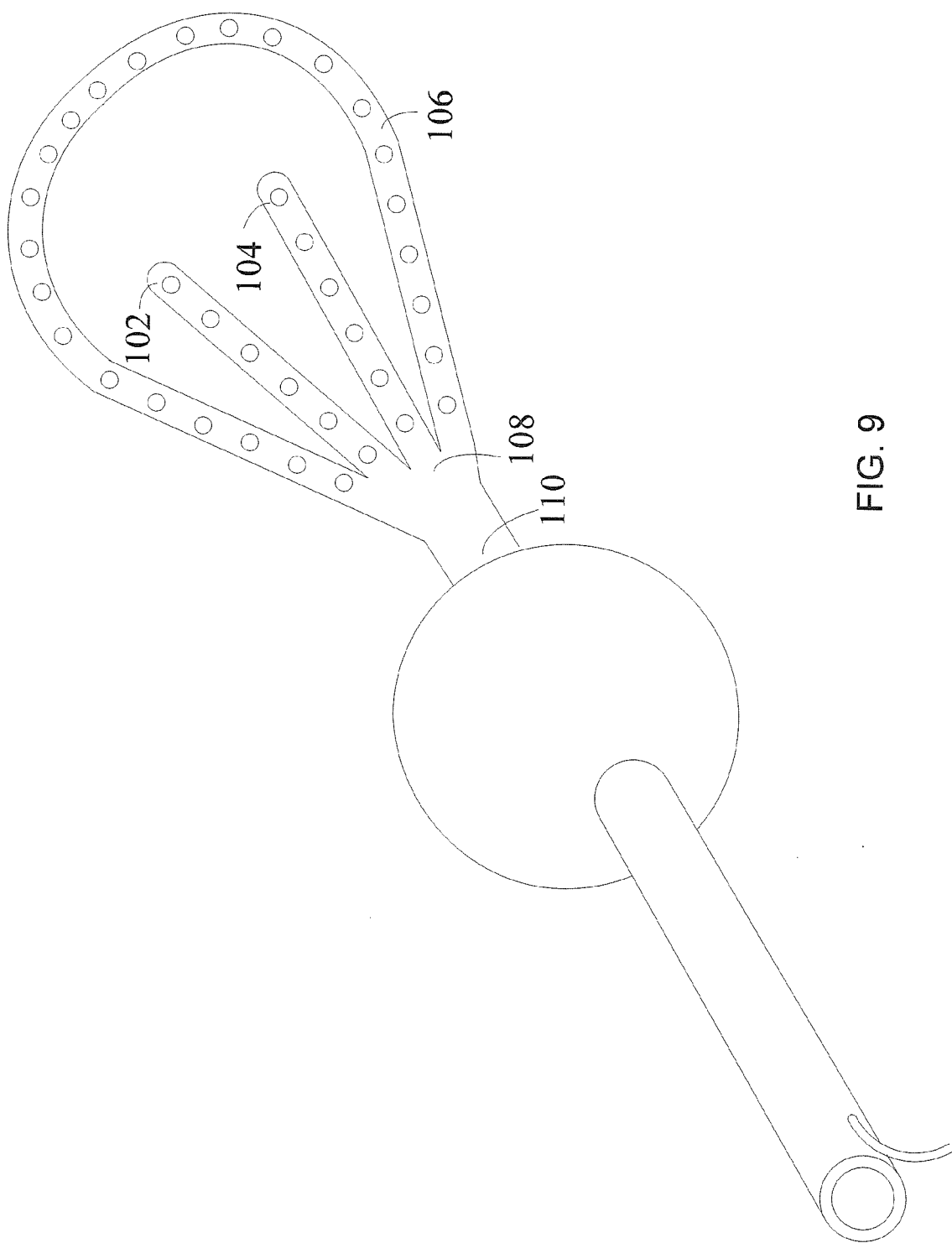
FIG. 9 is a perspective view of an embodiment of the uterine contractile device having perforated tubing in both elongated member and loop configurations.

FIG. 9 illustrates another alternate embodiment of the device (perspective view). In this embodiment, the array of tubes 102, 104, and 106 are a combination of previously described embodiments. The device may include one or more tubes in a loop configuration that have tubes that are coupled to two points and one or more tubes that extend from the connection tube 110 from a single connection point. All make an attachment 108 at the connecting tube 110. In an embodiment, the distance from a distal end of the tube 106 to the connecting tube 110 can be about 8.0-15.0 cm and the width of the connecting tube 110 in an uncompressed position can be about 4.0-9.0 cm. The length of the connecting tube 110 can be about 8.0-15.0 cm.

Operation of the Device

Figure 10:
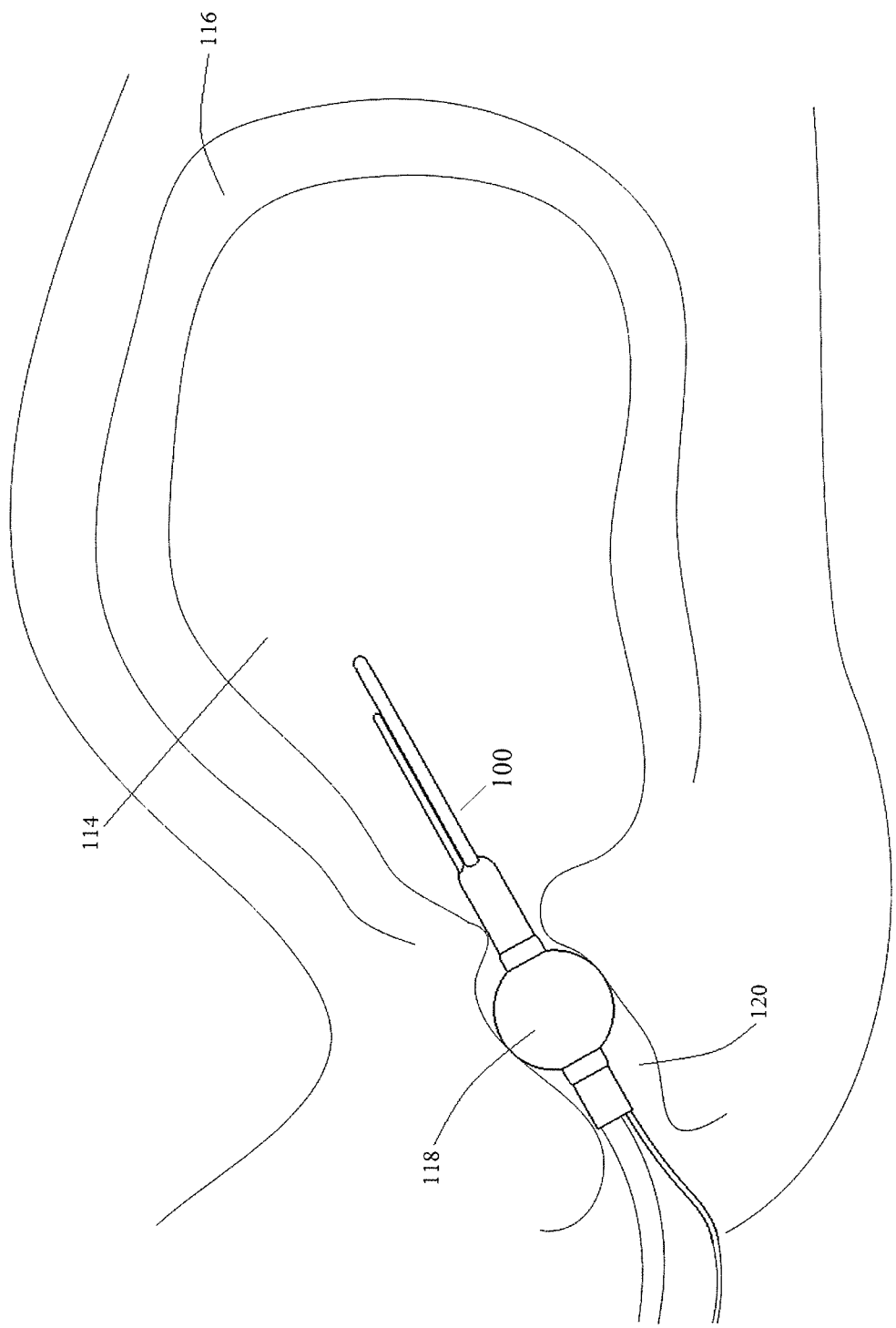
FIGS. 10-12 are cross sectional side views of a uterus with the uterine contractile device.
Figure 11:
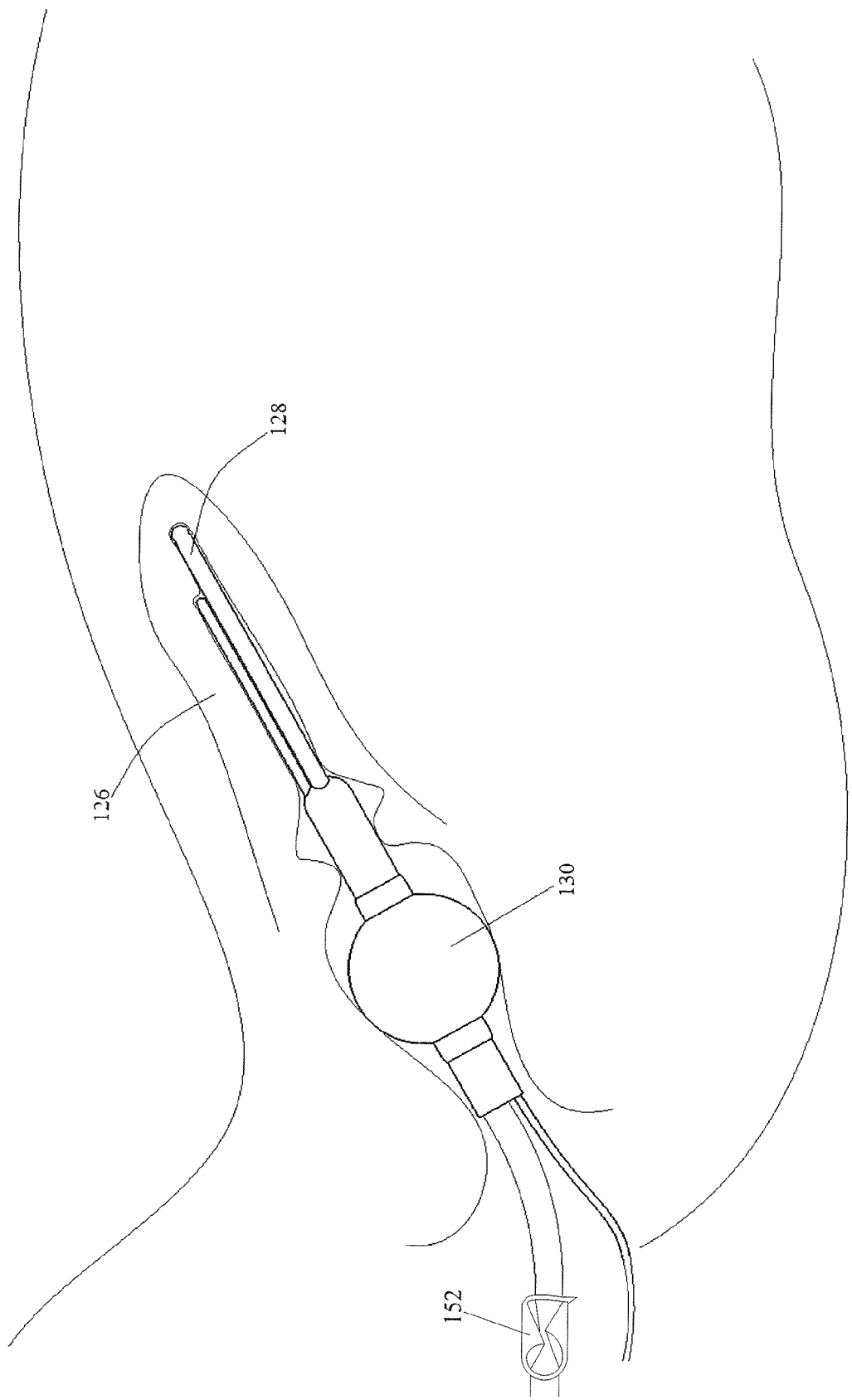

FIGS. 10-11 illustrate a sequence of cross sectional side views illustrating the implementation of the device 100 in a patient (side views). In FIG. 10, the device 100 is delivered transvaginally to the lumen 114 of the woman's atonic uterus 116, and the sealing balloon 118 is inflated near the distal end of the woman's vagina 120 to create a vacuum seal. In an embodiment, the sealing balloon 118 can be inflated to a pressure that can be about 0.1 to 5 psi. With reference to FIG. 11, the connecting tube is coupled to a vacuum mechanism and the vacuum is activated, causing the device 100 to remove fluid from the lumen 114 and causing the woman's uterus 116 to contract toward the device 100. Once the device 100 has fully sealed the uterus and suction has been initiated, the uterus may contract in a time from about 1.2 to 15 seconds. However, in other embodiments, a time frame of about 3 to 5 seconds may be more appropriate. A doctor can also monitor the contraction progress through a visual exterior assessment and/or with an ultrasound monitoring device which may be optional.

The process of contracting the uterine muscle will close exposed uterine arterioles in the uterine wall. In FIG. 11, the postpartum uterus 126 has been successfully contracted around the perforated tubing 128. The sealing balloon 130 may remain inflated as long as deemed necessary to maintain the uterine contraction. The device may be removed once a medical professional has determined that the mother's uterine muscles have recovered from their original fatigue. The process for removing the device 100 can comprise: clamping the suction tube 140 with a clamp mechanism 152 to seal the pathway and prevent gas or fluids from flowing back into the device 100 and uterus 126. The doctor(s) can then discontinue the suction being applied to the device 100. By maintaining the airtight seal in the uterus, the pressure differential is maintained, dramatically decreasing the possibility of the uterus returning to its atonic state. The device 100 should remain in the uterus for a period of at least 60 minutes and should be removed from the patient after no more than 24 hours. In an embodiment, the doctor may want to only remote the device 100 after the patient's blood pressure and heart rate return to normal levels. For example, the systolic blood pressure may need to be above about 90 mm Hg and below about 140 mm Hg and the heart rate may need to be above about 40 beats per minute and less than about 100 beats per minute.

Figure 12:
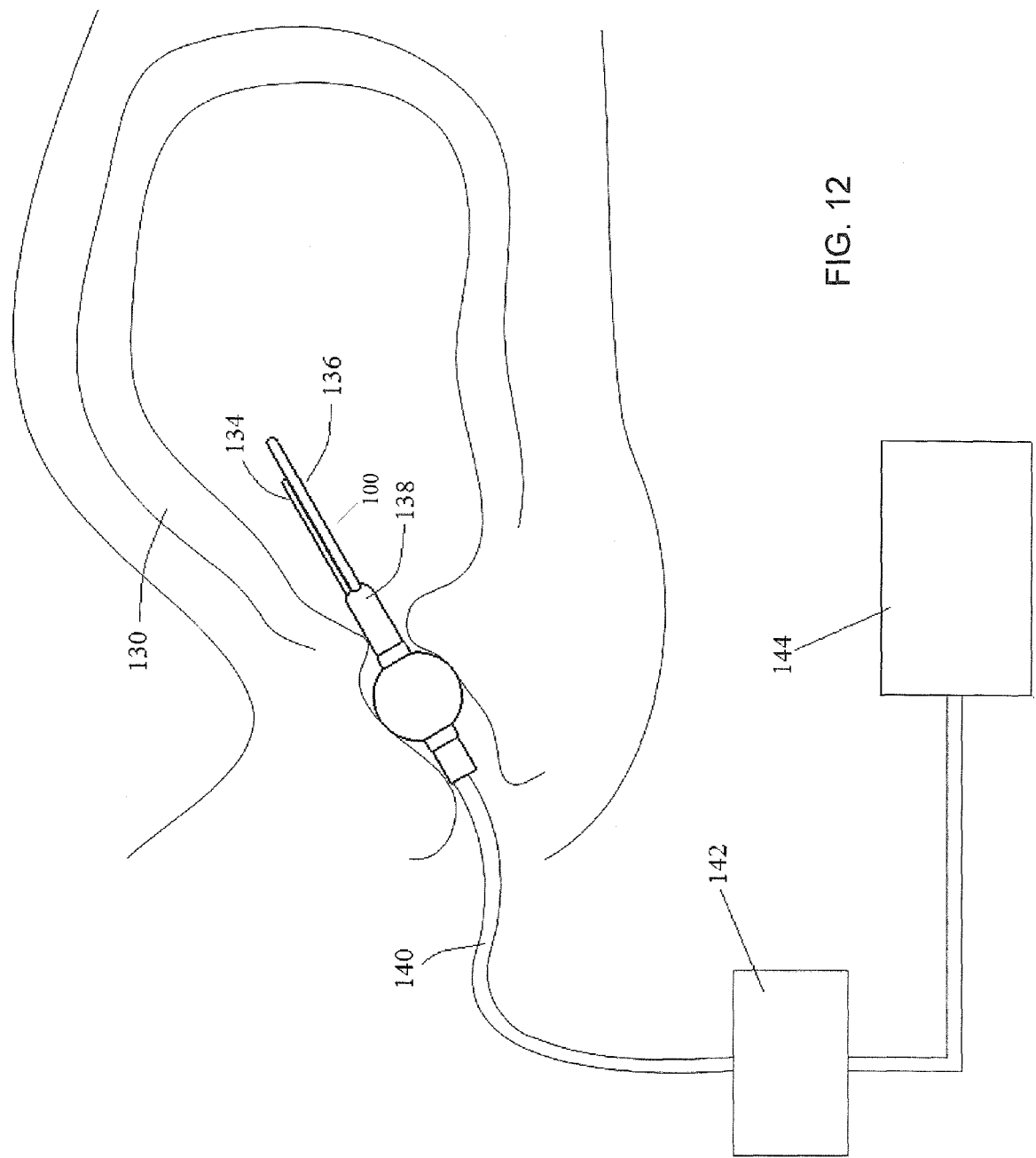

FIG. 12 illustrates a schematic of an embodiment of the device connected to external equipment. Air and other matter in the lumen of the postpartum uterus 130 passes through the perforated tubing 134 and 136 into the connecting tube 138. The vacuumed air then passes through a standard hospital suction line 140 into a standard fluid filter 142, allowing any collected blood or tissue to be removed from flow. The air finally passes into a standard hospital suction pump 144. This pump 144 can be operated over a range of flow rates, but preferably will be less than 30 liters per minute. The pressure inside the uterus will gradually drop to about 2 PSI below atmospheric pressure. At this point, the uterus will begin to contact slowly, depending on the flow rate of the pump 144.

The present disclosure, in various embodiments, includes components, methods, processes, systems and/or apparatus substantially as depicted and described herein, including various embodiments, subcombinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation. Rather, as the flowing claims reflect, inventive aspects lie in less than all features of any single foregoing disclosed embodiment.

We claim:

1. A method for contracting a uterus of a patient to counteract uterine atony, the method comprising:
providing a uterine contractile apparatus having a connecting tube, a set of flexible vacuum members coupled to the connecting tube, a sealing bladder surrounding the connecting tube, and an inflation tube coupled to the sealing bladder, each of the set of vacuum members having a perforated outer surface and an internal fluid passage;
positioning the set of vacuum members within the uterus and the sealing bladder near an entrance of the uterus, at an intravaginal canal location of the patient;
creating a seal configured to enable maintenance of a vacuum within the uterus, upon pumping a fluid through the inflation tube into the sealing bladder to inflate the sealing bladder;
creating the vacuum by way of the connecting tube and the set of vacuum members; and
contracting the uterus in order to counteract uterine atony, upon transmission of bodily fluids from the uterus through the set of vacuum members and the connecting tube, thereby mitigating uterine hemorrhaging.

2. The method of claim 1 further comprising:
maintaining the vacuum by way of the connecting tube and the set of vacuum members to contract the uterus until a rate of postpartum hemorrhaging is less than 5 milliliters per minute.

3. The method of claim 1 further comprising:
maintaining the vacuum by way of the connecting tube and the set of vacuum members to contract the uterus for at least 10 seconds.

4. The method of claim 1 further comprising:
maintaining the set of vacuum members within the uterus for at least 30 minutes.

5. The method of claim 1 further comprising:
transitioning between an inflated and a deflated state after positioning the sealing bladder near the entrance of the uterus.

6. The method of claim 1 further comprising:
filtering the bodily fluids removed from the uterus.

7. The method of claim 1 wherein the internal pressure of the sealing bladder after the pumping is between about 0.1 to 5 psi.

8. The method of claim 1 wherein the vacuum created is between 0.1 to 3 psi.

9. A method for contracting a uterus to counteract uterine atony comprising:
providing a uterine contractile apparatus having a connecting tube, a set of flexible vacuum members coupled to the connecting tube, a sealing bladder surrounding the connecting tube, and an inflation tube coupled to the sealing bladder, each of the vacuum members having a perforated outer surface and an internal fluid passage;
positioning the set of vacuum members within the uterus and the sealing bladder near an entrance of the uterus, at an intravaginal canal position;
pumping a fluid through the inflation tube into the sealing bladder to inflate the sealing bladder to create a seal, wherein the seal comprises a balloon, thereby sealing the entrance of the uterus at a position within the vaginal canal;
applying a vacuum to the connecting tube and the one or more vacuum members; and
contracting the uterus in order to counteract uterine atony, upon transmission of bodily fluids from the uterus through the one or more vacuum members and the connecting tube to remove the bodily fluids from the uterus, thereby mitigating uterine hemorrhaging.

* * * * *

UNITED STATES PATENT AND TRADEMARK OFFICE
CERTIFICATE OF CORRECTION

PATENT NO. : 9,550,014 B2
APPLICATION NO. : 13/420871
DATED : January 24, 2017
INVENTOR(S) : Alexander James Norred et al.

It is certified that error appears in the above-identified patent and that said Letters Patent is hereby corrected as shown below:

On the Title Page

Item (75), Inventors are corrected to read:
Alexander James Norred, San Luis Obispo, CA (US)
George Cochran Harper, Laguna Niguel, CA (US)
David Lagrew, Irvine, CA (US)
Davis Reed Carlin, San Luis Obispo, CA (US)

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*